United States Patent [19]

Swanbeck et al.

[11] Patent Number: 5,369,129
[45] Date of Patent: Nov. 29, 1994

[54] PREPARATION OF TOPICAL TREATMENT OF INFECTIONS CAUSED BY VIRUS, BACTERIA AND FUNGI

[75] Inventors: Gunnar Swanbeck, Askim; Jan Faergemann, Goteborg, both of Sweden

[73] Assignee: Hydro Pharma AB, Malmo, Sweden

[21] Appl. No.: 108,762

[22] Filed: Aug. 17, 1993

Related U.S. Application Data

[63] Continuation of Ser. No. 829,088, Feb. 13, 1992, abandoned.

[30] Foreign Application Priority Data

Jun. 13, 1989 [SE] Sweden ............................ 8902124-0

[51] Int. Cl.$^5$ ............................................. A61K 31/045
[52] U.S. Cl. ....................................................... 514/738
[58] Field of Search ............................................ 514/738

[56] References Cited

U.S. PATENT DOCUMENTS

| | | | |
|---|---|---|---|
| 3,291,580 | 12/1966 | Malick | 44/53 |
| 3,821,413 | 6/1974 | Hellger et al. | 424/343 |
| 3,836,672 | 9/1974 | Wright et al. | 424/343 |
| 3,970,759 | 7/1976 | Frankenfeld et al. | 424/343 |
| 4,173,653 | 11/1979 | Law | 424/333 |
| 4,612,169 | 9/1986 | Iwasaki et al. | 422/32 |
| 5,124,359 | 6/1992 | Wachman et al. | 514/642 |

FOREIGN PATENT DOCUMENTS 3430709 6/1986 Germany ................... A61K 31/045

OTHER PUBLICATIONS

Faergemann et al., *Sabouraudia*, 18, pp. 287-293 (1980).
Faergemann, *Current Therapeutic Research*, 43, No. 3, pp. 547-551 (Mar. 1988).
Herman et al., *Journal of Food Safety*, 2, pp. 131-139 (1980).
Herman et al. 94CA:702w 1981.

*Primary Examiner*—Marianne M. Cintins
*Assistant Examiner*—Russell Travis
*Attorney, Agent, or Firm*—Merchant, Gould, Smith, Edell, Welter & Schmidt

[57] ABSTRACT

A preparation for topical treatment of infections caused by virus, bacteria and fungi, said preparation contains pentane diol or hexane diol as active substance.

3 Claims, No Drawings

PREPARATION OF TOPICAL TREATMENT OF INFECTIONS CAUSED BY VIRUS, BACTERIA AND FUNGI

This is a continuation of application Ser. No. 07/829,088, filed Feb. 13, 1992.

BACKGROUND OF THE INVENTION

The present invention refers to a preparation for topical treatment of infections caused by virus, bacteria and fungi.

Diols or glycols are used as solvents, as anti-freezing agents or as vehicles in pharmaceutical preparations and some of them have an antimicrobial effect. A laboratory study of certain diols showed that the antimycotic activity was increased with an increasing length of the carbon chain.

So far propane-1,2-diol is the only diol widely used in dermatology. It is used in the treatment of Pityriasis versicolor, Pityrosporum folliculitis and Seborrhoeic dermatitis. It has even been active against Influenza A virus in vitro.

Certain laboratory tests indicate that pentane-1-5-diol has a higher activity against both fungi and bacteria than propane-1,2-diol (Faergemann et al: The antimycotic activity of five diols. Saubouradia 18:287–293, 1980). Nothing is however known about its effect in clinical treatment of infections caused by fungi and bacteria and nothing is known about its activity against virus, as far as we know. further has a low oral toxicity and is non-irritating to the skin.

There is today no effective topical treatment available for the treatment of recurrent herpes labialis. Acyclovir given orally is effective but no effective topical formulation has been found so far.

SUMMARY OF THE INVENTION

The object of the present invention is to provide a preparation that is effective in topical treatment of infections caused by virus, bacteria and fungi; especially herpes virus and Staphylococcus aureus and Staphylococcus epidermidis. This has been provided by using a composition containing pentane diol or hexane diol. Pentane-1,5-diol is a preferred diol.

DESCRIPTION OF THE INVENTION

Study 1: In the study described below we found that pentane-1,5-diol is effective in the treatment of recurrent herpes labialis.

In vivo experiments were performed on 17 patients, 15 females and 2 males (22–40 years old), culture positive for Herpes simplex virus Type I and with recurrent Herpes simplex virus infection. The patients had at least three recurrent infections per year.

Pentane-1,5-diol was diluted in ethanol to give a clear solution containing 50% pentane-1,5-diol and 50% ethanol. This solution was applied five times daily for 5 days starting as early as possible when the first small vesicles appeared. The lesions were assessed using a 0-3 scale where 0 means healed and 3 severe lesions. The parameters studied were: erythema, vesicles, ulcer and crusts. The patients were studied as early as possible after start of lesions and then after 5 days of treatment.

Result: Fifteen out of the 17 patients has one or several recurrent herpes labialis infections during a 4-6 month period. In 13 of the 15 patients only minor changes were seen at day 5, such as e.g. a slight erythema or a little crust. All of these patients claimed that the episode was milder than usual and that the pain often disappeared already on the first treatment day. They found the preparation effective, easy to use and no side effects were seen.

In the last two patients the treatment first started when larger vesicles had appeared and they experienced none or only a slight reduction in their lesions compared to previous infections.

Being effective against herpes labialis it is likely that pentane-1,5-diol is effective also against herpes genitalis. In vitro experiments were also performed by testing the effect of pentane-1,5-diol against fibroblast cells infected with Herpes simplex virus type I. Pentane-1,5-diol was cytotoxic against the fibroblasts used to culture Herpes simplex virus type I in a dilution of 1/100. In higher dilutions no effects were seen.

Thus its activity in vitro against Herpes simplex type I virus could not be evaluated because it was cytotoxic to the cells used to culture the herpes virus in as high dilution as 1/100.

Pentane-1,5-diol has a low oral toxicity; $LD_{50}$ for rats is 5.89 g/kg and $LD_{50}$ for rabbits is greater than 20 ml/kg. It is essentially non-irritating to the skin and only very mildly irritating to the eyes.

Study 2: In this study the activity of propane-1,2-diol and pentane-1,5-diol against certain bacteria were compared. The activity is given in Table 1 as MIC (%), i.e. the minimum concentration that gave a total inhibition of the growth of the bacteria. It is seen from Table 1 that pentane-1,5-diol had the highest activity against all of the bacteria tested.

TABLE 1

| Bacteria | MIC (%) | |
| --- | --- | --- |
| | Propane-1,2-diol | Pentane-1,5-diol |
| S. aureus | 20 | 5 |
| S. epidermidis | 20 | 5 |
| C. albicans | 10 | 4 |
| T. rubrum | 10 | 1 |
| P. ovale | 10 | 2 |

The above described studies refer to the use of pentane-1,5-diol, but it is likely that other pentane diols, hexane diol etc. have a corresponding effect. It is also likely that diols with longer carbon chains have a higher activity, but on the other hand they also have a higher toxicity. It is further likely that the diols according to the present invention have activity against infections caused by a variety of virus, bacteria and fungi. The concentration of the diol can vary from a high dilution to concentrated form.

We claim:

1. A method for treating an infection caused by herpes viruses, which comprises the step of:
   (a) topically administering a composition comprising a pentane diol or hexane diol to the infection.

2. A method according to claim 1, wherein the composition comprises pentane-1,5-diol.

3. A method according to claim 1, wherein the composition further comprises a solvent selected from water.

* * * * *

UNITED STATES PATENT AND TRADEMARK OFFICE
CERTIFICATE OF CORRECTION

PATENT NO. :   5,369,129

DATED      :   Nov. 29, 1994

INVENTOR(S) :  Swanbeck et al.

It is certified that error appears in the above-identified patent and that said Letters Patent is hereby corrected as shown below:

On title page, item [30], insert,
--PCT/SE 90/00406, June 12, 1989--.
On title page, item [30], insert,
-- June 12, 1989  PCT  SE90/00406 --.
In column 1, line 7, insert --abandoned-- after the year "1992".

Signed and Sealed this

Tenth Day of September, 1996

Attest:

BRUCE LEHMAN

Attesting Officer        Commissioner of Patents and Trademarks